United States Patent [19]

Woodard

[11] Patent Number: 5,405,951
[45] Date of Patent: Apr. 11, 1995

[54] SOLID PHASE EXTRACTION PURIFICATION OF DNA

[75] Inventor: Daniel L. Woodard, Raleigh, N.C.

[73] Assignee: Becton Dickinson and Company, Franklin Lakes, N.J.

[21] Appl. No.: 81,485

[22] Filed: Jun. 23, 1993

Related U.S. Application Data

[63] Continuation of Ser. No. 695,113, May 3, 1991, abandoned.

[51] Int. Cl.⁶ ............................................. C07H 1/06
[52] U.S. Cl. ................. 536/25.41; 536/25.4
[58] Field of Search ................ 536/25.4, 25.41; 435/270

[56] References Cited

U.S. PATENT DOCUMENTS

| | | | |
|---|---|---|---|
| 4,830,969 | 5/1989 | Holmes | 536/25.4 |
| 4,900,677 | 2/1990 | Hewitt | 536/25.4 |
| 4,923,978 | 5/1990 | McCormick | 536/25.4 |
| 4,935,342 | 1/1990 | Seligson et al. | 536/25.4 |
| 4,946,952 | 8/1990 | Kiefer | 536/25.4 |
| 5,075,430 | 12/1991 | Little | 536/25.4 |

OTHER PUBLICATIONS

B. Vogelstein et al., *Proc. Natl. Acad. Sci. U.S.A.* 76:615 (1979) R. McCormick, *Analytical Biochemistry* 181:66 (1989).
M. Marko et al., *Analytical Biochemistry* 121:382 (1982).
S. Chow et al., *Analytical Biochemistry* 183:42 (1989).
R. Boom et al., *J. Clin. Microbiol.* 28:495 (1990).
O. Barsotti et al., *Ann. Inst. Pasteur/Microbiol.* 138:529 (1987).
O. Yameda et al., *Journal of Virological Methods* 27:203 (1990).

*Primary Examiner*—Douglas W. Robinson
*Assistant Examiner*—James O. Wilson
*Attorney, Agent, or Firm*—David W. Highet

[57] ABSTRACT

The invention provides a method for purifying DNA from any source in any form. The method comprises the use of water soluble organic solvents when purifying DNA. By using water soluble organic solvents such as ethanol, propanol, and isopropanol, DNA is purified with greater recovery amounts. In addition, the use of water soluble organic solvents eliminates the use of caustic and poisonous compositions such as chaotropes.

15 Claims, No Drawings

SOLID PHASE EXTRACTION PURIFICATION OF DNA

This application is a continuation of application Ser. No. 07/695,113, filed May 3, 1991, now abandoned.

FIELD OF THE INVENTION

The invention is in the field of molecular biology. In particular, the invention is in the area of deoxyribonucleic acid purification.

BACKGROUND OF THE INVENTION

The continued advances in molecular biology and related disciplines present continued needs for improvements in tools associated with fully appreciating and developing the advanced technology.

A wide range of technologies involve the use of deoxyribonucleic acids (DNA) in a variety of forms. For example, advances in the area of recombinant DNA technology continually require the use of DNA in the form of probes, genomic DNA, and plasmid DNA.

Advances in the area of diagnostics also continue to utilize DNA in a variety of ways. For example, DNA probes are routinely used in the detection and diagnosis of human pathogens. Likewise, DNA is used in the detection of genetic disorders. DNA is also used in the detection of food contaminants. And, DNA is routinely used in locating, identifying and isolating DNA of interest for a variety of reasons ranging from genetic mapping to cloning and recombinant expression.

In many instances DNA is available in extremely small amounts, and isolation and purification procedures can be laborious and time consuming. The often time consuming and laborious procedures can lead to loss of DNA. In the purification of DNA from specimens obtained from serum, urine, and bacterial cultures, there is the added risk of contamination and false-positive results.

Typical DNA purification protocols involve the use of caustic and poisonous compositions. The typical DNA purification protocol uses high concentrations of chaotropic salts such as sodium iodine and sodium perchlorate.

There are numerous protocols for purifying DNA. As evidenced by recent activity in the area of DNA purification, there is a continued pursuit for optimal DNA purification protocols. U.S. Pat. No. 4,923,978 discloses a process for purifying DNA in which a solution of protein and DNA is passed over a hydroxylated support and the protein is bound and the DNA is eluted. U.S. Pat. No. 4,935,342 discloses purification of DNA by selective binding of DNA to anion exchangers and subsequent elution. U.S. Pat. No. 4,946,952 discloses DNA isolation by precipitation with water-soluble ketones. A DNA purification procedure using chaotropes and dialyzed DNA is disclosed in U.S. Pat. No. 4,900,677.

While the present protocols for purifying DNA are able to accomplish their goal, it is desirable to purify DNA without the use of such caustic and poisonous compounds such as the most often used chaotropes in addition to obtaining increased amounts of DNA.

SUMMARY OF THE INVENTION

The present invention provides a method for purifying DNA which comprises the use of non-caustic and nonpoisonous solvents.

In one embodiment is provided a method for purifying DNA from solution which comprises the addition of a water soluble organic solvent to attach DNA to hydrophilic surfaces.

In a preferred embodiment is provided a method for purifying DNA from solution which comprises:
(a) addition of a hydrophilic surface to the solution,
(b) adding a water soluble organic solvent,
(c) separating the DNA solution comprising (a) and (b) into a liquid and non-liquid fraction,
(d) washing the non-liquid fraction of (c),
(e) separating the liquid fraction from the non-liquid fraction in (d), and
(f) removing DNA from the non-liquid fraction of (e).

The invention is especially useful in obtaining greater amounts of purified DNA. In addition, DNA can be purified by binding any hydrophilic surface. Also, the purification can conveniently be performed at room temperature.

The present invention can be practiced by substituting water soluble organic solvents for the binding buffer suggested in any DNA purification protocol. "Purifying", as used in this document refers to obtaining DNA substantially free of cellular debris, and the like.

DETAILED DESCRIPTION OF THE INVENTION

The start of any DNA purification or isolation procedure requires obtaining the desired DNA from its source. Typical protocols for obtaining DNA from specimens such as serum, urine and bacterial cultures are well known and routinely carried out. Likewise, the ability to obtain DNA from genomic libraries and the like are routine.

The present invention is directed toward the purification of DNA that has been obtained from the particular source. Where the DNA originated is not the key to practicing the invention. The key to the invention is the ability to purify DNA, once obtained from its source. Typical procedures for obtaining DNA end with a suspension of the DNA in solution. References include those for isolation of DNA from biological samples, Harding, J. D., Gebeyehu, G., Bebee, R., Simms, D., Ktevan, L., *Nucleic Acids Research*, 17:6947 (1989), and Marko, M. A., Chipperfield, R., and Birnboim, H. C., *Analytical Biochemistry*, 121:382 (1982). Procedures for isolation of plasmid DNA can be found in Lutze, L. H., Winegar, R. A., *Nucleic Acids Research* 20:6150 (1990). Extraction of double-stranded DNA from biological samples can be found in Yamada, O., Matsumoto, T., Nakashima, M., Hagri, S., Kamahora, T., Ueyama, H., Kishi, Y., Uemura H., Kurimura, T., *Journal of Virological Methods* 27:203 (1990). Most DNA solutions comprise the DNA in a suitable buffer such as TE (Tris-EDTA), TEA buffer (40 mM Tris-Acetate, 1 mM EDTA), or a lysate.

Once the DNA is obtained in a suitable solution, a binding matrix is typically added to the solution. Generally used binding matrixes are silica in the form of glass or diatoms.

After a binding matrix has been added to the solution of DNA, a binding buffer is added. The present invention uses a binding buffer that is a water soluble organic solvent. The term "water soluble organic solvent" refers to a solvent that has organic characteristics that results in DNA leaving solution.

Preferred steps for practicing the invention with hydrophilic surfaces of particles, beads, and the like, comprise a binding step, a washing step, a drying step and an elution step. The binding step generally comprises the addition of a hydrophilic surface to a DNA containing solution, addition of a solution comprising water soluble organic solvent (order of addition of hydrophilic surfaces or water soluble organic solvent is not critical), agitation, centrifugation, and discarding the liquid fraction. The binding step is usually repeated at least once. The wash step generally comprises the addition of a wash buffer to remove solvent (for example 50% ethanol and 50% (40 mM Tris, 4 mM EDTA, 0.8 N NaCl pH 7.4)), agitation, centrifugation, and the discarding of liquid. The drying step generally comprises drying for about 2 to 20 minutes at about 40–70 degrees C. The elution step generally comprises the addition of an elution buffer (to remove DNA from surface: for example (10 mM Tris, 1 mM EDTA, pH 8.0), vortexing for about 30 seconds, heating for about 10 minutes at about 40–70 degrees C, centrifuging for about 2 minutes and collecting the liquid. At this point the liquid contains the DNA. The elution step is usually repeated at least once.

When practicing the invention with hydrophilic surfaces like filters, preferred steps include a binding step, a wash step, and an elution step. The binding step generally comprises the addition of a water soluble organic solvent to a DNA containing solution, adding through a filter the resultant solution (typically to a well of a blotter or any other filtration system (e.g., syringe filtration)), and optionally passing a water soluble organic solvent through the filter. The filter is briefly air dried (about one minute) after filtering. The wash step generally comprises the addition of a buffer (to remove solvent) through the filter. Generally the filter is briefly air dried (about a minute). The elution step generally comprises removal of DNA from the filter. The area of the filter that was in contact with the solutions is cut out and put in a centrifuge tube. An elution buffer (to remove DNA from filter) is then added followed by heating at about 40–60 degrees C for about 10 minutes. The liquid, which now contains the DNA, is then removed.

Suitable water soluble organic solvents include ethanol, propanol, isopropanol, and acetonitrile. Various concentrations of water soluble organic solvents can also be used in practicing the invention. Preferably the solvent is 100% isopropanol, ethanol or propanol. Most preferably the solvent is isopropanol. Suitable concentrations of water soluble organic solvents include 1% to 100% solutions of ethanol, propanol, isopropanol and acetonitrile. Preferably the concentrations are 20% to 80%. Most preferably the concentrations are 40% to 60%. Typically the variable concentration of solvent is reduced with water, however, combinations of the solvents can also be used. Preferred combinations of solvents include isopropanol and ethanol, isopropanol and propanol, and propanol and ethanol.

Binding matrixes suitable for use in practicing the invention include any hydrophilic surface. Examples of hydrophilic surfaces suitable for use in practicing the invention include nitrocellulose, celite diatoms, silica polymers, glass fibers, magnesium silicates, silicone nitrogen compounds (e.g., SIN4), aluminum silicates, and silica dioxide. The variety of forms that the hydrophilic surfaces can take are also suitable for use in the invention. Suitable forms of hydrophilic surfaces include beads, polymers, particles, and filters (i.e., membranes).

Binding buffers such as the well known chaotropes are believed to cause DNA in solution to attach to hydrophilic surfaces due to the hydration of the chaotrope. The hydration of the chaotrope is believed to reduce the interaction of water molecules with the DNA. The DNA, in turn, is believed forced into interaction with water molecules surrounding the hydrophilic surfaces which results in the DNA attaching to the hydrophilic surface through hydrogen bonding.

While not wishing to be bound or limited by theory, it is believed the present invention reduces the aqueous character of the DNA solution by using a water soluble organic solvent as a "binding buffer". By reducing the aqueous character of the DNA solution it is believed the DNA is forced to interact with the hydrophilic surfaces, thereby effecting a solid phase extraction. In addition, as demonstrated in the Examples section of this document, the invention results in purification by way of binding to a hydrophilic surface and not by way of precipitation.

The invention can be used to purify DNA from a variety of sources and from a variety of forms. Sources of DNA for purification include bacteria, bacteriophage, specimens, plants, animals, and the like. DNA can be found in a variety of forms and includes single-stranded, double-stranded, circular, and linear. The invention can be practiced with DNA from any source in any form.

The following examples illustrate the specific embodiments of the invention described in this document. As would be apparent to skilled artisans, various changes and modifications are possible and are contemplated within the scope of the invention described.

EXAMPLE 1

This experiment compares binding properties of different binding buffers to 6M NaClO$_4$ (prep-a-gene). All experiments are in a prep-a-gene matrix (Prep-a-gene kit, Bio-Rad, Richmond, CA) performed under the same conditions except for the substitution of binding buffers.

| Materials: | | LOT # |
|---|---|---|
| Polyethyleneglycol (PEG) | Fluka (Fluka Chemical Corp, Ronkon, NY) | 24718584 MW |
| Urea | Fisher (Fisher Scientific, Norcross, GA) | 895704 |
| KSCN (potassium thiocyanate) | Sigma (Sigma Chemical Co., St. Louis, Mo.) | 488-0409 |
| Ethanol (E + OH) | Fisher | 902233 |
| Butanol (BuOH) | Fisher | 890783 |
| Glycerol | Sigma | 104F-0026 |
| Guanidine Hydrochloride | BRL | 9DB209 |
| Sodium Hydroxide (NaOH) | Fisher | 862699 |
| Ammonium Hydroxide (NH$_4$OH) | Fisher | 860118 |
| Sulfuric Acid (H$_2$SO$_4$) | Fisher | 860102 |
| Acetonitrile (CH$_3$CN) | Fisher | 890789 |
| Sodium Acetate (NaOAc) | Sigma | S-2889 lot 19F-0010 |
| Prep-a-gene kit | BioRad | Control 41180 |
| λDNA (503μg/803μL) | BRL (Bethesda Research Labs, Ground Island,NY) | 56125A |

Procedure:

All 13 binding buffers were used with the same conditions.

To each of the thirteen samples was added 20 μL of prep-a-gene diatom solution, followed by 750 μL of binding buffer lightly vortex and incubate 5 minutes at 45 degrees C, centrifuge 2 minutes, discard supernate and repeat binding step. Wash with 500 μL of wash buffer, centrifuge, discard buffer and repeat. Add 25 μL elution buffer, vortex, incubate 5 minutes at 50 degrees C., centrifuge, save supernate, repeat. Gel was run on each of the thirteen samples and the one standard.

The following binding buffers are listed in order of use:

1) Standard 6M NaClO4 (sodium perchlorate) from the prep-a-gene kit
2) 10% PEG
3) 20% PEG
4) 6M Glycerol
5) 95% EtOH
6) 100% BuOH
7) 6M KSCN
8) 6M Urea
9) 8M Gaunidine HCl
10) 30% NH4OH
11) 10% H2SO4
12) 100% CH3CN
13) 6M NaOAc
14) Standard λ DNA Results of gel electrophoresis of the 13 eluted DNA samples compared to the original DNA sample (λDNA) shows ethanol is superior to the 6M sodium perchlorate and all other binding buffers tested for retention of DNA on the solid phase (Prep-a-gene matrix). Acetonitrile was also good.

EXAMPLE 2

This experiment expands the results obtained in Example 1. In that experiment EtOH and CH3CN were shown to be good DNA binding buffers. In this experiment it will be determined how low the % of ethanol, CH3CN and MeOH can be in the binding buffer and still get good separation or recovery of the DNA. All experiments are done using the prep-a-gene matrix.

| Materials: | |
| --- | --- |
| Prep-a-gene kit | BioRad |
| EtOH | Fisher |
| MeOH | Fisher |
| CH3CN | Fisher |
| 1% agarose gel | |

λ DNA BRL 56125A, 9 Mol 104 503 μg in 803 μL
Experimental 15 fractions/experiments were done differing only in the binding buffer used. The wash buffer, elution buffer and solid phase were all from a prep-a-gene kit. The procedure is performed in substantial accordance with the teaching of Example 1. 1.3 μl λ DNA is used in each fraction.

| Fractions (diluted with H2O if not 100%): | | |
| --- | --- | --- |
| 1) 100% EtOH (aq) | 6) 100% MEOH (aq) | 11) 100% CH3CN (aq) |
| 2) 80% EtOH (aq) | 7) 80% MEOH (aq) | 12) 80% CH3CN (aq) |
| 3) 60% EtOH (aq) | 8) 60% MEOH (aq) | 13) 60% CH3CN (aq) |
| 4) 40% EtOH (aq) | 9) 40% MEOH (aq) | 14) 40% CH3CN (aq) |
| 5) 20% EtOH (aq) | 10) 20% MEOH (aq) | 15) 20% CH3CN (aq) |

The eluted DNA from the fifteen tested fractions was analyzed by gel electrophoresis and compared to a standard DNA sample (1.3 μL of λ DNA in 48 μL TE buffer (10 mM Tris HCl 1 mM EDTA, pH8.0)). Results indicate 100% ethanol is the best binding buffer with 100% acetonitrile the second best. The more organic character imparted to the binding buffer results in better DNA retention.

EXAMPLE 3

This experiment compares the binding abilities of propanol (PrOH), isopropanol (iPrOH) and ethanol (EtOH) and dilutions thereof to each other as well as to NaClO4. The purpose being to optimize the organic effect on the binding of DNA to prep-a-gene matrix.

| Materials: | | |
| --- | --- | --- |
| Prep-a-gene kit | BioRad | Control (kit) 41492, Matrix 40523 |
| λDNA (503 μg/803μL) | BRL 56125A, 9MOL 104 | |
| 1% agarose gel | | |
| EtOH | Fisher | 902233 |
| PrOH | Fisher | 744241 |
| iPrOH | Aldrich | 06208TW |
| DMSO (dimethylsulfoxide) | Aldrich | 9624HC |

Procedure:

13 fractions were done. See below for binding buffer used in each of the 13 fractions. All were done with prep-a-gene kit materials, except binding buffers, and prep-a-gene procedure in substantial accordance with the teachings of Example 1.

Binding Buffers Used:
1) 100% propanol
2) 80% propanol 20% H2O
3) 100% isopropanol
4) 80% isopropanol 20% H2O
5) 100% DMSO
6) 80% DMSO 20% H2O
7) 20% propanol 80% ethanol
8) 40% propanol 60% ethanol
9) 60% propanol 40% ethanol
10) 20% isopropanol 80% ethanol
11) 40% isopropanol 60% ethanol
12) 60% isopropanol 40% ethanol
13) Prep-a-gene binding buffer 6M NaClO4
14) Standard DNA (λ DNA)

The eluted DNA samples were analyzed by gel electrophoresis and compared to the standard DNA sample. Results indicate 100% Isopropanol is the best binding buffer. 100% propanol also resulted in good DNA retention. Isopropanol and propanol can be diluted to about 80% in water and still retain DNA. The tests indicate that as the % of isopropanol or propanol in the ethanol dilutions is increased, the amount of DNA retained is also increased.

A lot of the highest weight DNA (closest to well where DNA started) is retained with iPrOH (100%), this is higher than with any other binding buffer used. DMSO retained no DNA.

The following summarizes binding buffers' ability to retain DNA with preferences listed from best to worst based on analysis by gel electrophoresis compared to standard:

| Retains DNA | No Retentions |
|---|---|
| 1) iPrOH | 10% PEG |
| 2) EtOH | 20% PEG |
| 3) 6M NaClO4 | 6M glycerol |
| 4) 60% iPrOH 40% EtOH | 6M Urea |
| 5) 60% PrOH 40% EtOH | 30% NH4OH |
| 6) PrOH | 10% $H_2SO_4$ |
| 7) A) 40% iPrOH 60% EtOH | 6M NaOAC |
| B) 40% PrOH 60% EtOH | |
| 8) A) 80% iPrOH 20% $H_2O$ | MeOH 100% or |
| B) 80% PrOH 20% $H_2O$ | agueous dilutions |
| 9) A) 20% PrOH 80% EtOH | EtOH less than 100% |
| B) 20% PrOH 80% EtOH | |
| 10) 8M guanidine HCl | $CH_3CN$ less than 100% |
| 11) 6M KSCN | DMSO less than 100% |
| 12) $CH_3CN$ | |
| 13) NaI | |
| 14) BuOH | |
| 15) 6M Guanidine HSCN | |
| 16) 6M $(NH_4)_2SO_4$ | |
| 17) 6M NaCl | |

EXAMPLE 4

This experiment compares the binding buffers 6M $NaO_3Cl$ and iPrOH in their ability to stick DNA to a variety of glass fiber membranes.

Materials:
Gelman Sciences, Inc. filter (Gelman Sciences, Ann Arbor, MI) Type AE glass filter (Lot 603202).

MSI glass fiber filter (Micron Separation, Inc., West Borl, MA) (Lot 19571).

Whatman GF/B (Whatman Ltd., England, UK) Control 7823 Whatman GF/D (Control 4706).

Whatman GF/C (Control 1505). λ DNA (BRL) Lot 9 mo 1104 (503 μg/803 μL) Nitrocellulose (Schleicher & Schuell, Keene, NH) 44031621 Prep-a-gene (Bio-Rad) control 4004.

| iPrOH | Fisher | 744241 |
|---|---|---|

Equipment:
Blotter (Bio/Dot apparatus by Bio-Rad)

Procedure:
Six (6) fractions were prepared identical to each other except that the membrane used to trap the DNA was different in each case. About 1.3 μλ DNA is dissolved in about 248 μL TE buffer. This is diluted with about 750 μL iPrOH and added to the blotter by passing through the filter. After all the liquid is pulled through, air dry about 1 minuteN Add about 750 μL iPrOH again air dry about 1 minute. After all iPrOH is pulled through, add about 750 μL of prep-a-gene wash buffer, pull through and air dry about 1 minute.

Cut the filter where the well comes through. Put cut out portion in centrifuge tube. Add 50 μL prep-a-gene elution buffer. Heat at about 60° C. for about 20 minutes. Results from gel electrophoresis show isopropanol superior for Whatman GF/B, Whatman GF/C, MSI glass, Gelman AE and nitrocellulose. Isopropanol and Gelman AE filters retained about 100% of the DNA.

EXAMPLE 5

This experiment determines 1) the effect of pH on DNA binding 2) the effectiveness of CELITE (diatomaceous earth or diatoms) as a binding surface and 3) the effect iPrOH has on DNA sticking to silanized surfaces (i.e., hydrophobic).

Materials:
Silanized surfaces
Prep-a-gene
iPrOH
1N NaOH
1N HCl
1% agouse gel in 1xTE buffer
TE buffer
Loading dye
λ DNA Procedure:
7 samples with 248 μL TE buffer and 1.3 μL λ DNA are made. To samples 1–3 is added 1 of 3 silanized surfaces (prep-a-gene matrix, gene-clean matrix (Bio101, La Jolla, CA, and circle prep matrix (Bio 101)) followed by 750 μL iPrOH. Heat at 60° C. for 10 minutes.

During this time, to 3 samples add 20 μL prep-a-gene matrix and to the 4th add 20 μL of a solution of 50% celite 545 (Fisher) and 50% TE buffer. To the celite sample and 1 of the other 3 samples add 750 μL prep-a-gene binding buffer, to 1 sample add 750 μL of prep-a-gene binding buffer pH 11.0, adjusted with 1N NaOH. To one sample add 750 μL prep-a-gene binding buffer pH .1, adjusted with 1N HCl. Heat all 4 for 10 minutes at 60° C.

Centrifuge the 7 samples and decant the binding buffer. Add 750 μL of the same binding buffer to each sample that was used the first time on that sample. Heat at 60° C. for 5 minutes. Centrifuge and decant binding buffer. To each sample add 500 μL prep-a-gene elution buffer, stir/shake 5 minutes, centrifuge, decant, dry at 60° C. for 10 minutes. Add 25 μL prep-a-gene wash buffer, heat at 60° C. for 10 minutes, centrifuge, collect buffer, repeat the elution step.

The eluted fractions were analyzed by gel electrophoresis and compared to standard DNA samples. The results demonstrate that no DNA is recovered from the silanized surfaces, thus, in previous experiments the DNA bound to the surfaces and was not precipitated (a precipitate would not bind the surfaces and would wash away in the wash step).

EXAMPLE 6

This experiment compares binding buffer ability to bind DNA to nitrocellulose membranes.

Starting Materials:
Wash buffer (50% EtOH 50% (40 mM Tris 4 mM EDTA 6M NaCl pH 7.4))
Binding buffer (50 mM Tris 1 mM EDTA, 6M NaClO4 pH7.5)
Elution buffer (10 Mmol Trios 1 mM EDTA pH8.0)
Nitrocellulose (5.0 μM AE98 Order #19020 Lot 643317 S&S)
Nitrocellulose (.45 μm BA85 lot #9039/7 S&S)
1% agouse gel in 1X TAE(1X=89 mM Tris-Borate,2 mM EDTA, 89 mM
Boric Acid)
Loading dye
TE buffer
iPrOH
EtOH KSCN
8M guanidine HCl
TBS buffer
NaClO4
Prep-a-gene kit
Procedure:

7 identical samples are made (248 μL TE buffer and 1.3 μL λ DNA). The 7 samples are bound to nitrocellulose membranes using a blotter with exact same procedures as described in Example 4, except for a different binding buffer used each time.

The DNA solution is added to 750 μL of the binding buffer then added to a well. Pull the liquid through and air dry 1 minute. Add 750 μL of the respective binding buffer to the well, pull through and air dry 1 minute. Wash with 750 μL of wash buffer. Pull through and air dry 1 minute.

Cut out the circle below each well and put in a centrifuge tube. Add 50 μL elution buffer, heat at 60° C. for 10 minutes The eluted DNA samples were analyzed by gel electrophoresis and compared with standard DNA samples. Results show that isopropanol, propanol, and ethanol retain DNA while the chaotropes retain significantly less DNA.

EXAMPLE 7

The purpose of this experiment is to determine if λ DNA spiked into a Chlamydia lysate will bind to diatoms using isopropanol as the binding buffer.
Materials
  Isopropanol (Aldrich, Milwaukee, WI 02610 MW)
  Prep-a-gene kit (BioRad 41640)
  λ DNA -(BRL 503 μg/803 μL)
  Chlamydia (−) lysates:
  Chlamydia (−) lysates from Wake County Health Dept.
  TE buffer (10 mM Tris-HCl, 1 mM EDTA, pH 8)
  TAE buffer (1X)
  Ethidium Bromide (10 mg/1 ml stock (Sigma Cat #E-875 Lot #97E-3722)
  4% NuSieve agarose in 1xTAE Buffer
  ΦX 174 RF DNA/Hae III (BRL Cat #5611SA Lot #940103)
  λ DNA/Hind III (BRL Cat #5612SA Lot #9M0104)
  Type II Loading Dye (25% Ficoll, 0.25% Bromophenol Blue, 0.25% Xylene cyanol)

| Electrophoresis Unit: | BRL Horizon 58 Submarine Unit |
|---|---|
| Power Unit: | Pharmacia Type EPS 500/400 |
| Photo Equipment: | Polaroid Type 50 Land Camera Polaroid Type 57 Film Fotodyne Light Box UV |
| Other: | Siliconized Sterilized Microcentrifuge Tubes Gel/Loading Pipet Tips (Stratagene, LaJolla, CA). |

Sample, Preparation and Procedure:

13 samples are made, each containing ~250 μL of one of the Chlamydia (−) human samples listed. To each of these samples is added 10 μL of 1:10 dilution of the λ DNA sample. A 14th sample is made containing 250 μL H2O and 10 μL of the 1:10 dilution of λ DNA, no Chlamydia (−) human sample is added.

To 5 of the samples and the standard are added 20 μL of prep-a-gene loading matrix followed by 750 μL isopropanol, shake at room temperature 10 minutes. To the remaining 8 samples the isopropanol is added first followed by binding matrix and shaking. The remainder of the experiment was done exactly the same for all 13 samples and the standard.

After shaking samples at room temperature for 10 minutes, centrifuge 1 minute, decant and discard supernate. Wash with 750 μL isopropanol, shake at room temperature 10 minutes, centrifuge, decant and discard supernate. Heat at 50 degrees Centigrade 10 minutes to dry binding matrix. Add 25 μL prep-a-gene elution buffer. Heat at 50 degrees Centigrade 10 minutes, centrifuge 1.5 minutes. Collect supernate, repeat elution step combining eluted factions of each of the 14 samples giving 14 (50 μL) eluted DNA samples. These eluted samples are analyzed by gel electrophoresis to determine if any DNA was eluted.

The experiment demonstrates that DNA can be removed from a sample containing cellular debris (i.e., carbohydrates, proteins, nucleic acids, etc). Both the control λ DNA and human DNA are removed from the sample. The experiment also demonstrates that a number of different protocols can be used with isopropanol as the binding buffer and still get a large percentage of DNA removed from a sample (e.g., heat can be applied in the binding step, or not, two binding steps can be used or one, a wash step can be used with 50% ethanol and 50% low concentration EDTA pH8.0 buffer or no wash. The order of addition of reagents is unimportant, in other words, binding buffer or binding matrix may be added first with no significant changes in the amounts of DNA recovered from the respective sample).

Although the invention has been described with respect to specific modifications, the details thereof are not to be construed as limitations, for it will be apparent that various equivalents, changes and modifications may be resorted to without departing from the spirit and scope thereof, and it is understood that such equivalent embodiments are to be included therein.

What is claimed is:

1. A method for purifying DNA from solution in the absence of chaotropes which comprises:
  a) adding to the solution (i) a hydrophilic surface selected from the group consisting of celite diatoms, silica polymers, magnesium silicate, silicon nitrogen compounds, aluminum silicates, silica dioxide, glass fiber and nitrocellulose, and (ii) a water soluble organic solvent selected from the group consisting of 80–100% isopropanol, 80–100% propanol, 95–100% ethanol, 100% acetonitrile, and mixtures consisting essentially of 20–80% of each of at least two alcohols selected from the group consisting of isopropanol, propanol and ethanol;
  b) allowing the DNA to bind to the hydrophilic surface:
  c) separating the hydrophilic surface with the bound DNA from the solution;
  (d) washing the separated hydrophilic surface with the bound DNA, and;
  (e) eluting the DNA from the hydrophilic surface with an elution buffer.

2. The method of claim 1 in which a combination of the solution, organic solvent and hydrophilic surface is agitated prior to separation of the hydrophilic surface.

3. The method of claim 1 in which steps (a), (b) and (c) are repeated at least once prior performance of steps (d) and (e).

4. The method of claim 1 in which washing step (d) is repeated at least once.

5. The method of claim 1 in which the hydrophilic surface is celite diatoms.

6. The method of claim 1 in which the hydrophilic surface is silica dioxide.

7. The method of claim 1 in which the hydrophilic surface is aluminum silicates.

8. The method of claim 1 in which the water soluble organic solvent is 100% isopropanol.

9. The method of claim 1 in which the water soluble organic solvent is 100% propanol.

10. The method of claim 1 in which the water soluble organic solvent is 100% ethanol.

11. The method of claim 1 in which the water soluble organic solvent is about 80% isopropanol and about 20% water.

12. The method of claim 1 in which the water soluble organic solvent is about 80% propanol and about 20% water.

13. The method of claim 1 in which the water soluble organic solvent is about 60% isopropanol and about 40% ethanol.

14. The method of claim 1 in which the water soluble organic solvent is about 60% propanol and about 40% ethanol.

15. The method of claim 1 which further comprises heating to elute the DNA.

* * * * *